United States Patent
Shvets et al.

(10) Patent No.: US 7,439,072 B2
(45) Date of Patent: Oct. 21, 2008

(54) APPARATUS AND METHOD FOR DROPLET MEASUREMENTS

(75) Inventors: Igor Shvets, Dublin (IE); Alexander Shvets, Dublin (IE); Sergei Makarov, Dublin (IE); Juergen Osing, Dublin (IE); Cecilia Franken, Dublin (IE)

(73) Assignee: Allegro Technologies Limited, Dublin (IE)

( * ) Notice: Subject to any disclaimer, the term of this patent is extended or adjusted under 35 U.S.C. 154(b) by 722 days.

(21) Appl. No.: 10/787,229

(22) Filed: Feb. 27, 2004

(65) Prior Publication Data

US 2005/0223814 A1 Oct. 13, 2005

(51) Int. Cl.
*G01N 25/08* (2006.01)

(52) U.S. Cl. .................................... 436/150
(58) Field of Classification Search ............... 73/170.17, 73/861.08; 436/150; 422/100
See application file for complete search history.

(56) References Cited

U.S. PATENT DOCUMENTS

| | | | | |
|---|---|---|---|---|
| 3,389,601 | A * | 6/1968 | Semplak | 73/170.17 |
| 4,706,509 | A * | 11/1987 | Riebel | 73/865.5 |
| 4,896,099 | A * | 1/1990 | Suzuki | 324/667 |
| 5,414,609 | A * | 5/1995 | Levran et al. | 363/17 |
| 6,439,068 | B2 * | 8/2002 | Windolph | 73/865.5 |

FOREIGN PATENT DOCUMENTS

EP 1099484 A1 * 5/2001

* cited by examiner

*Primary Examiner*—Walter D. Griffin
*Assistant Examiner*—Bobby Ramdhanie
(74) *Attorney, Agent, or Firm*—Birch, Stewart, Kolasch & Birch, LLP

(57) ABSTRACT

There is provided a liquid droplet monitoring and measuring apparatus (1) for a liquid droplet dispensing system having a nozzle (5) with a dispensing tip (7). The apparatus (1) comprises an inner chamber (2) surrounded by an outer shield (3), preferably not in contact with each other. An RF oscillator electrically energizes the liquid through an electrode (11). The inner chamber (2) is connected through pre-amplifiers (16), band pass filters (17conditioning amplifier (20) to a signal read-out device (21). The operation of the apparatus is based on the measurement of the capacitance between the nozzle (5) and the inner chamber (2). As a droplet (15) grows on the dispensing tip (7), the capacitance between the nozzle (5) and the inner chamber (2) increases. Therefore, the signal detected and received by the signal read-out device (21) changes. This change is directly related to the volume of the droplet which can therefore be measured. In another embodiment, the liquid is not energized but is used to change the dielectric constant of a capacitor formed by, for example, the nozzle (5) and a substrate.

32 Claims, 14 Drawing Sheets

APPARATUS AND METHOD FOR DROPLET MEASUREMENTS

FIELD OF THE INVENTION

The present invention relates to a liquid droplet monitoring and measuring apparatus for use with a droplet dispenser of the type comprising a nozzle having a dispensing tip and means for delivering the liquid under pressure through the nozzle onto a receiving substrate. Further, the invention provides a method of monitoring and measuring the volume of a liquid droplet as it is being dispensed from a liquid dispensing system comprising a nozzle having a dispensing tip.

BACKGROUND OF THE INVENTION

The present invention is generally related to liquid handling systems for dispensing and aspirating small volumes of liquids of the order of 1 ml and smaller and in particular of the order of 50 microliters and smaller. Liquid handling systems are being provided and will be provided in the future for the dispensation of droplets of even smaller sizes. The present invention is particularly directed to liquid handling systems used in life science, medical and pharmaceutical sectors for applications such as high throughput screening, microarraying, Polymeraze Chain Reaction (PCR), combinatorial chemistry, proteomics, protein crystallography, genetic screening and others. The invention may also be used for medical diagnostics e.g. for printing reagents on a substrate covered with bodily fluids or for printing bodily fluids on substrates. The technology may also be used for applications outside the life science, medical and pharmaceutical sectors. For example it may be used for dispensing small volumes of lubricants for precision micromachining and drilling, and also for dispensing of small volumes of adhesives for the microelectronics industry and micromechanics and other applications.

The development of instrumentation for dispensing minute volumes of liquids has been an important area of technological progress for some time. Numerous devices for dispensing of small volumes of liquids of the order of 50 microliters and smaller have been developed over the past twenty-five years.

The requirements of a dispensing system vary significantly depending on the application. For example the main requirement of a dispensing system for ink jet applications is to deliver a droplet of a fixed volume with a high repetition rate. The separation between individual nozzles making up the ink jet dispenser should be as small as possible so that a number of nozzles may be accommodated on a single printing cartridge. On the other hand the task is simplified by the fact that the properties of the liquid dispensed, namely ink, are well defined and consistent.

For life science, medical and pharmaceutical applications the requirements are completely different. The system should be capable of handling a variety of liquids with different mechanical properties, e.g. viscosity. For many such applications it is important to be able to freely adjust the volume dispensed. Recent inventions related to the field of small volume liquid handling are covered by numerous patent applications, e.g. U.S. Pat. No. 5,744,099 (Chase et al); U.S. Pat. No. 4,574,850 (Davis); U.S. Pat. No. 5,035,150 (Tomkins), U.S. Pat. No. 5,741,554 (Tisone); U.S. patent application Ser. No. 09/709,541 (Shvets et al) filed 13 Nov., 1990, PCT patent Application No. /IE02/00039 (Shvets et al), filed 26 Mar. 2002, U.S. patent application Ser. No. 09/816, 326 (Shvets et al) filed Mar. 26, 2001 and also described in scientific and technical publications [I. Schneider, Nanoliter Dispensing, Drug Discovery and Development, June 2002, p 51-54;

J. Comley, Nanoliter Dispensing—on the Point of Delivery, Drug Discovery World, Summer 2002, p 33-44;

D. Rose, Microdispensing Technologies in Drug Discovery, Drug Discovery Technology, vol 4, N9, September 1999, p 411-419;

S. D. Rose, Applications of a Novel Microarraying System in Genomics Research and Drug Discovery, Journal of the Association for Laboratory Automation, vol 3, N3, 1998, p 53-56;

I. V. Shvets, S. Makarov, C. Franken, A. Shvets, D. Sweney, J. Osing, Spot on Technology of low volume liquid Handling, Journal of Association of Laboratory Automation, vol 7, N 6, December 2002, p 127-131].

The wide variety of the mechanical properties of liquids and the very nature of many biological liquids often make consistent dispensing difficult. For example the dispenser can be easily blocked by a cloth as these are readily formed in cell-based liquids and protein solutions. Therefore, it is highly desirable to be able to verify that the instrument is dispensing correctly and in many cases to be able to detect the moment when the dispenser runs out of the liquid. It is also desirable to be able to detect if the liquid handling instrument leaks or if a drop fails to separate from the dispensing nozzle of the instrument. Additionally, in many instances, it is advantageous to be able to measure the volume of the droplet dispensed to ensure that it does correspond to the amount requested by the operator of the dispensing system. Independent verification of the volume dispensed becomes more and more important as the users have to operate in an environment of increasing legal regulation. For example, failure to dispense a drop may lead to an incorrect result of a medical test and consequently to incorrect diagnosis. Therefore, the user requirement for availability of such measurement technologies for operation verification intensifies.

It is also desirable for manufacturers of various liquid handling instruments to have in-house instrument test and calibration tools. During the production phase and also during the phase of development of new liquid handling instruments, it is important to have tools for quality control, calibration, tuning and optimisation of the instruments.

The issue of droplet volume measurement for small volume dispensing is also important from a psychological point. The reason is that in many cases the operator cannot readily monitor visually arrival of a tiny drop to a destination substrate, in particular, if the destination substrate is not flat. This adds to the user discomfort even if the dispenser functions properly as the user cannot readily satisfy himself/herself in this by simple visual monitoring.

It is difficult to fulfil challenging requirements for a successful system for measurement of droplet volume during dispensing. For many applications the ideal system must measure the volume in non-contact mode meaning that direct transfer of the drop to a measurement device such as microbalance is not an option.

U.S. Pat. No. 5,559,339 (Domanik) teaches a method for verifying a dispensing of a liquid droplet of relatively large size from a nozzle. The method is based on coupling of light from a source to a receiver. As a droplet of liquid travels from the nozzle it obstructs the coupling and therefore, the intensity of the signal detected by the receiver is reduced. The disadvantage of this method is that it is based on the absorption of electromagnetic radiation (in practice light) by the droplet. It will therefore not work for liquids that do no absorb the radiation well. For a range of applications where minute droplets of liquids with a broad range of optical properties need to be dispensed, the method may be inappropriate. Those familiar with the fundamentals of scattering of electromagnetic radiation by an object will readily appreciate that in order for this method to work, the wavelength of the electromagnetic radiation needs to be smaller than the droplet size.

Another method of volume measurement is based on detection of a charge carried by a droplet. The droplets are typically charged by applying a high voltage to the dispenser. The charge carried by the droplet depends on the droplet's size. In some inventions it is proposed using a Faraday pail for this purpose (U.S. patent application Ser. No. 09/709,541, filed 13 Nov., 1990 (Shvets et al); PCT/IE02/00039, filed 26 Mar. 2002 (Shvets et al); U.S. patent application Ser. No. 09/816,326 filed Mar. 26, 2001 (Shvets et al)). Faraday pails are well known and described in many published documents (see for example, Industrial Electronics by D. M. Taylor and P. E. Secker, Research Studies Press, 1994 ISBN) 0-471-1523333-8 and Electrostatics: Principles, Problems and Applications by J. Cross, A. Hilger ISBN 0-85274-589-3). Essentially the Farad The shield and the box are well insulated from each other. In this situation a charged droplet arriving at the box induces a charge of the opposite sign and same magnitude at the surface of the box. This charge is created by the current flowing to the inner box and it can be measured by a charge measurement circuit. Generally the dispenser and hence the nozzle are maintained at a relatively high voltage. The shield and box are connected to ground potential. The charge can also be measured without catching the droplet in the pail. For this the pail is made in the shape of a cylinder without a bottom. Thus the charged droplets progress through the Faraday pail that serves as an induced charge detector. The Faraday pail can be used to detect the moment when the droplet enters into the box and leaves it. Therefore, it can be used to measure the droplet's velocity, as the length of the box is known.

The Faraday pail has a number of disadvantages. One of the disadvantages is that it is sensitive to external electromagnetic noise, e.g. noise at 50 or 60 Hz frequency. To measure the volumes of small drops, the sensitivity of the Faraday pail must be optimised meaning that the entry and exit holes of the shield and the inner box must be reduced in size. This increases the chances of missing the exit hole and thus leaving the drop attached to the wall of the inner chamber. Another disadvantage is that in order to increase the charge carried by the droplet and thus improve the sensitivity of the instrument, it is often necessary to apply as high a voltage to the dispenser as possible. This may create further complications; e.g. the risk of destroying a charge sensitive amplifier connected to the pail, the risk of the malfunctioning of high voltage equipment with consequent danger for the operator, etc.

In some cases there is further complication related to the size of the drop. The liquid is often ejected from a dispenser in the form of a jet. If the total volume of the jet is small enough, the jet can then form a single drop as it travels through the air. This happens under the influence of the surface tension that favours the spherical shape over the cylindrical one. If the volume of the jet is rather large, the surface tension can alternatively split the jet into a number of drops. The length of the jet segment could be considerable even for relatively small volume of liquid ejected from the dispenser. For example, a 200 nl volume ejected from a nozzle with the diameter of 0.152 mm turns into a 11 mm long jet segment. This could be comparable to the size of the pail and therefore add to inaccuracy of the drop volume measurement as the jet segment can no longer be considered as a small charge surrounded from all the sides by the inner chamber of the Faraday pail.

To summarise, at present the issue of reliable detection and measurement of the volume of droplets dispensed is still not entirely resolved. It is suggested that the lack of a commonly acceptable measurement technology impedes wider use of low-volume liquid handling equipment.

OBJECTS OF THE INVENTION

The present invention is directed towards providing a method and apparatus for the monitoring of the dispensation and the measurement of volumes of liquids in the range from less than 0.1 Nanoliter to over 100 microliters.

The invention is further directed towards measurement of the volume during dispensing from a dispensing device.

Another objective is to measure the volume of the drop during flight as it travels from the dispenser to the destination location. The aim here is to measure the volume of the drop in the non-contact mode, i.e. so that the drop does not come in contact with the measuring device.

Another objective of the invention is to provide a method and apparatus for detection of the timing of the beginning and end of the dispensing and also verification of a single dispensing event.

Another objective is to provide a method and apparatus for verification that there is not leakage from the dispenser.

Yet another objective is to provide a method and apparatus for monitoring whether or not the liquid is left at the end of the dispensing tip of the nozzle of the dispenser after the dispensation, i.e. monitoring if a hanging drop develops at the dispenser.

Another objective is to provide a method and apparatus for detection of dispenser blockage and when the dispenser runs out of liquid.

Yet another objective is to provide the method of monitoring the velocity of the jet ejected by the dispenser.

Yet another objective is to provide the device and method that could confirm arrival of the nozzle of dispenser to the dispensing position.

SUMMARY OF THE INVENTION

The invention provides a method of monitoring and measuring the volume of a liquid droplet as it is being discharged from a liquid dispensing system comprising a nozzle having a dispensing tip. The method involves using the liquid to form at least part of one of the three components of the capacitor, namely, the dielectric and the two separate electrically conductive members. Then the change in capacitance in the capacitor so formed is measured as the liquid is discharged from the nozzle. Thus, the volume of the liquid dispensed and the termination of the discharge may be recorded. Obviously, this is because the liquid droplet may form one of the electrically conductive members of the capacitor or alternatively the liquid droplet forms the dielectric member and is positioned in the vicinity of the electrically conductive members of the capacitor and thus alters the effective dielectric constant of the capacitor.

The invention utilises the fact, often overlooked, that in a typical low volume non-contact mode dispenser, the drop is often ejected in the elongate droplet rather than a sphere. In accordance with the invention, one can electrically energise the liquid with AC current and measure the capacitance induced in an electrically conductive member sited adjacent the tip as the liquid is being discharged from the nozzle.

When the liquid and nozzle are of a high electrical conductivity, the method envisages the provision of an electrode remote from and beneath the nozzle. Then the nozzle and the electrode form plates for what is the capacitor whereby the growth of a droplet on the dispensing tip increases the capacitance until it drops on detachment of the droplet from the dispensing tip.

In accordance with the invention, when the liquid is a water based liquid, the liquid is energized at a carrying frequency ($f_o$) of between 100 KHz and 5 MHz or indeed may be between 0.1 KHz and 1 MHz.

In another method according to the invention, the liquid is energized with both AC and DC current and the volume of the liquid is calculated from both the change in capacitance and the charge carried by the liquid droplet. With this latter method, when the variance between the calculated volumes exceeds a preset amount, a possible malfunction may be recorded.

Various calibration methods may be performed. Generally, they entail dispensing a plurality of droplets, measuring the change in capacitance in accordance with the invention, weighing the droplets and storing the data for subsequent use. Thus, close correlation can be provided easily between the change in capacitance and the volume of the droplet.

Sometimes, liquid is delivered from a nozzle in a continuous jet and the jet forms separate droplets remote from the dispensing tip. This occurs while still maintaining the jet. In this case, the invention envisages measuring the change in capacitance caused by the jet immediately before and after the formation of a droplet to determine the volume and other characteristics of the droplet.

Ideally, the information on the characteristics of the droplets is used to control the manner in which the jet is formed. Also, the invention can be used to determine whether a leak is occurring in the apparatus since when liquid is not being discharged, if a change in capacitance is sensed, then this indicates a leak.

In one method according to the invention, the nozzle is sited within a conductive chamber having an outlet to allow the passing of the liquid therethrough from the nozzle dispensing tip. Then, the liquid is energized by applying a voltage at a preset carrying frequency ($f_o$) to it. Finally, the capacitance induced by the interaction of the liquid and the chamber is measured until the liquid detaches from the nozzle.

In this method according to the invention, when the liquid and nozzle are of high electrical conductivity, there is provided an electrode remote from and beneath the nozzle, the nozzle and electrode forming plates for the capacitor whereby the growth of the droplet on the dispensing tip increases the capacitance until it drops on detachment of the droplet from the dispensing tip.

It is also envisaged that a capacitor may be provided and then the liquid droplets are directed into the vicinity of the capacitor whereby the dielectric constant of the capacitor is sufficiently changed to provide a measurable change in the capacitance sensed which in turn allows the volume of the liquid droplet to be determined.

In another embodiment, the actual chamber in which the liquid is discharged may itself be a capacitor.

Further, the invention provides a liquid droplet monitoring and measuring apparatus for use with a droplet dispenser of the type hereinbefore described. The apparatus will have an electrically conductive member and means for mounting the electrically conductive member adjacent the dispensing tip. Then there is provided means for electrically energising the liquid with AC current. Finally, means are provided for measuring the change in capacitance between the electrically conductive member and the liquid droplet, as the liquid droplet is being formed on and subsequently detached from the dispensing tip.

In one embodiment of the invention, the means for energising the liquid is a radio frequency (RF) oscillator.

In another embodiment, the electrically conductive member comprises a cylindrical chamber.

In another embodiment, instead of a cylindrical chamber, it is an open-ended sleeve having an entrance for reception of a nozzle and an exit for discharge of a droplet, almost certainly onto a substrate.

In another embodiment of the invention, the nozzle is electrically conductive and the electrically conductive member is mounted beneath the dispensing tip and spaced-apart therefrom. Thus, the nozzle and the electrically conductive member form the plates or electrodes of the capacitor.

In another embodiment of the invention, there is provided additional means for energising the liquid with both AC and DC current and means for sensing when the droplet exits the apparatus.

In another embodiment of the invention, the apparatus comprises a capacitor formed from a pair of spaced-apart electrically conductive plates. Then the capacitor is mounted adjacent the dispensing tip, whereby the delivery of liquid out of the nozzle changes the dielectric constant of the capacitor.

In another embodiment of the invention, the capacitor may be formed from two simple electrodes or conducting plates which are sited adjacent the nozzle.

DETAILED DESCRIPTION OF THE INVENTION

The invention beneficially utilises the often overlooked fact that in a typical low volume non-contact mode dispenser the drop is often ejected in the form of a jet segment or elongate drop or droplet rather than a sphere. As explained above, the sphere is then formed out of the segment due to surface tension. It is true to say that if the pressure difference at which the drop is ejected is low, the drop can still grow in sphere-like shape at the end of the nozzle. However, in this case the drop tends to remain attached to the nozzle up to a relatively large volume per drop dispensed. Therefore, to achieve detachment of the drop from the nozzle, the drop often needs to be a ejected at a relatively high pressure and thus it forms a jet. For more details on this one can consult the specifications of the following patent applications, namely: U.S. patent application Ser. No. 09/709,541 (Shvets et al), filed 13 Nov., 1990; PCT patent Application No. PCT/IE02/00039 (Shvets et al), filed 26 Mar. 2002; and U.S. patent application Ser. No. 09/816,326 (Shvets et al) filed Mar. 26, 2001, the disclosures of which are included herein by way of reference. While the main purpose and object of the present invention is to determine the volume of the droplet dispensed, a further and important object, as explained above, is to determine the timing of the beginning and end of the dispensing and such matters as the verification of a single dispensing event. All these other factors are included under the general term "characteristics". Thus, for example, it might be very important to determine not just simply the volume of a droplet being dispensed, but the rate at which the droplets were being dispensed because this can, in many instances, determine the pressure and manner in which the droplets are dispensed.

Figure 1:
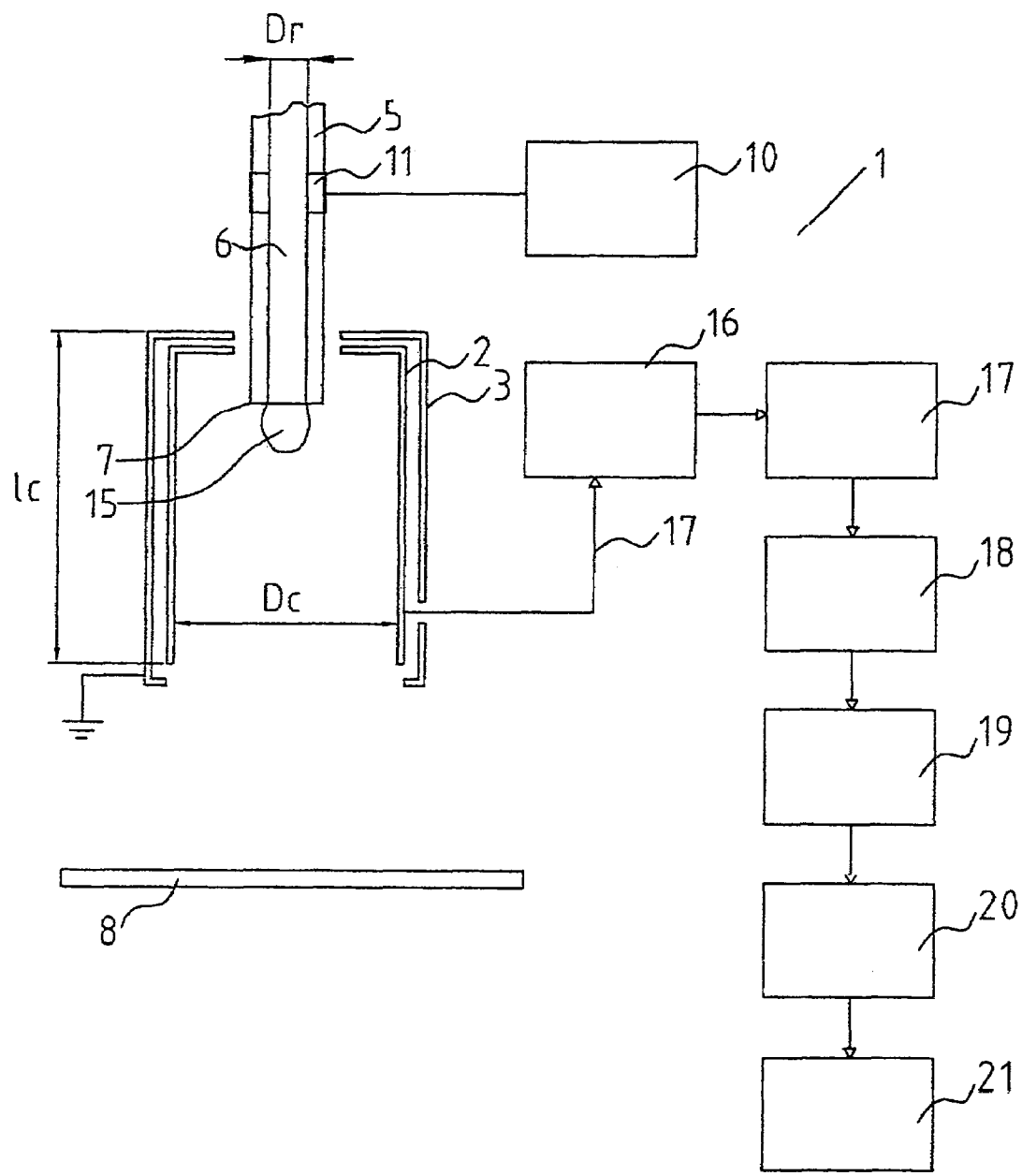
FIG. 1 is a diagrammatic representation of a liquid monitoring and measurement apparatus of the invention with portion of the liquid dispensing system.

Referring to the drawings and initially to FIG. 1 there is illustrated a liquid monitoring and volume measuring apparatus of the invention, indicated generally by the reference numeral 1. The apparatus 1 comprises an inner chamber 2 and outer shield 3 that are preferably not in electric contact with each other. In a typical embodiment the inner diameter $D_c$ of the inner chamber is $D_c=2$ to 5 mm and its length is $l_c=2$ to 8 mm. The outer shield 3 is made so that it covers the inner chamber 2 closely to avoid any parasitic electromagnetic pickup coming from outside the instrument. Both the inner chamber 2 and the outer shield 3 are made of a conducting material. In this embodiment, a nozzle 5 of a dispenser which is not shown as its specific construction has no relevance to the invention, is placed inside the inner chamber. The nozzle 5 has a bore 6 of diameter Dr terminating in a dispensing tip 7. The dispenser nozzle 5 is of an electrically insulating material.

In FIG. 1, the nozzle 5 of the dispenser is shown elongated. It should be kept in mind that in certain dispensing systems, the nozzle in fact is not elongated. This point is not significant for the present invention and both elongated and short nozzles may be used with the present invention. For the clarity and ease of reading the figures, the nozzles in all the figures are shown elongated.

The dispenser could be any suitable dispenser utilising by way of example and without limitation positive displacement pump technology, magnetic floating boss technology, piezo-electric materials-based technology, or technology based on solenoid valves. A destination substrate 8 in this embodiment is positioned underneath the chamber 2. The destination substrate 8 could be a well plate, flat polymer, metal or glass substrate, test strip, test tube or indeed any other suitable substrate.

The outer shield 3 is kept at a fixed potential, e.g. at ground potential. The output from a radio frequency (RF) oscillator 10 is connected to the dispenser nozzle. The radio frequency oscillator 10 is connected to an electrode 11 embedded in the nozzle 5 for direct electrical contact with liquid in the nozzle 5. The electrode 11 is then guided through the wall of the nozzle 5 to the RF oscillator 10 so that electrical contact is established with the liquid inside it. If the nozzle 5 is made of electrically insulating material, then it will be appreciated that it is not necessary to provide the electrode 11 as the entire nozzle serves as such an electrode. The liquid is energized by an AC voltage at the frequency $f_o$ that is called hereinafter the carrying frequency. A droplet, identified by the reference numeral 15, is also energized as it is formed on the dispensing tip 7. Thus, the droplet 15 maintains this charge at the carrying frequency $f_o$ until it detaches from the nozzle. In a typical embodiment the frequency $f_o$ is 0.1 to 1 MHz. The amplitude of the signal at the output of the RF oscillator coupled to the nozzle is typically in the range of 0.1-20 V. The inner chamber 2 is connected to a fast, low bias current preamplifier 16 by means of a suitable cable such as e.g. coaxial cable or twisted pair in this embodiment a coaxial cable 17.

The output of the preamplifier 16 is connected to a band-pass filter 17 that passes through the signals only within a frequency window around carrying frequency. The typical bandwidth of the band-pass filter is about 5 to 100 kHz. The purpose of the band-pass filter 17 is to reject all the other frequency components, that may add unwanted noise (e.g. 50 Hz power line interference) and do not belong to the useful signal bandwidth. The required bandwidth allows passing the amplitude-modulated signal, that carries the information about the droplet dispensed with time resolution down to approximately 5 to 20 us.

The output of the band-pass filter 17 is connected to a precision high speed full-wave rectifier 18. The rectifier 18 converts the signal from the band pass filter 17 into its absolute value. For example if a voltage $A*\sin_\omega t$ is sent to the rectifier 18, it is then converted into the voltage $|A*\sin_\omega t|$, i.e. the signal is unchanged for positive voltage values and reversed for negative voltage values.

After rectification the signal is sent from the rectifier 18 to a low-pass filter 19. In a typical embodiment the low-pass filter cuts off all the frequencies above 5 to 100 KHz.

The signal from the output of the low-pass filter 19 is sent to a signal-conditioning amplifier 20 and then to the readout device 21, in this embodiment an oscilloscope. The pulse height is detected and may be calibrated in μl units as described below.

The operation of the apparatus 1 is based on measurement of capacitance between the nozzle 5 and the inner chamber 2. As the droplet 15 grows on the dispensing tip 7 at the end of the nozzle 5, the capacitance between the nozzle 5 and the inner chamber 2 increases. Therefore, the signal at the carrying frequency detected by the preamplifier 16 increases. Unlike in the Faraday Pail, the operation is not based on measurements of the static charge carried by the droplet. The capacitance changes as the droplet 15 grows at the end of the nozzle 5. As the droplet 15 gets detached from the dispensing tip 7, the capacitance drops even if the droplet 15 is still located inside the inner chamber 2. This is a major difference between the operation of the present invention and the Faraday pail.

In the Faraday pail the signal induced is essentially unaffected by the separation of the droplet from the nozzle and affected by the droplet leaving the inner box. This is because the droplet maintains the charge once it gets detached from the nozzle. In the present invention on the contrary the signal is affected by the separation of the droplet from the nozzle and relatively insensitive to the droplet leaving the inner chamber. This is because the capacitance between the nozzle and inner chamber changes dramatically once the separation of the droplet occurs.

It will be appreciated that in the embodiment above, there are many ways in which electrical contact with the liquid may be established. It can obviously be established through the wall of a non-conducting dispenser by means of any type of feed through electrode or the like.

Figure 2:
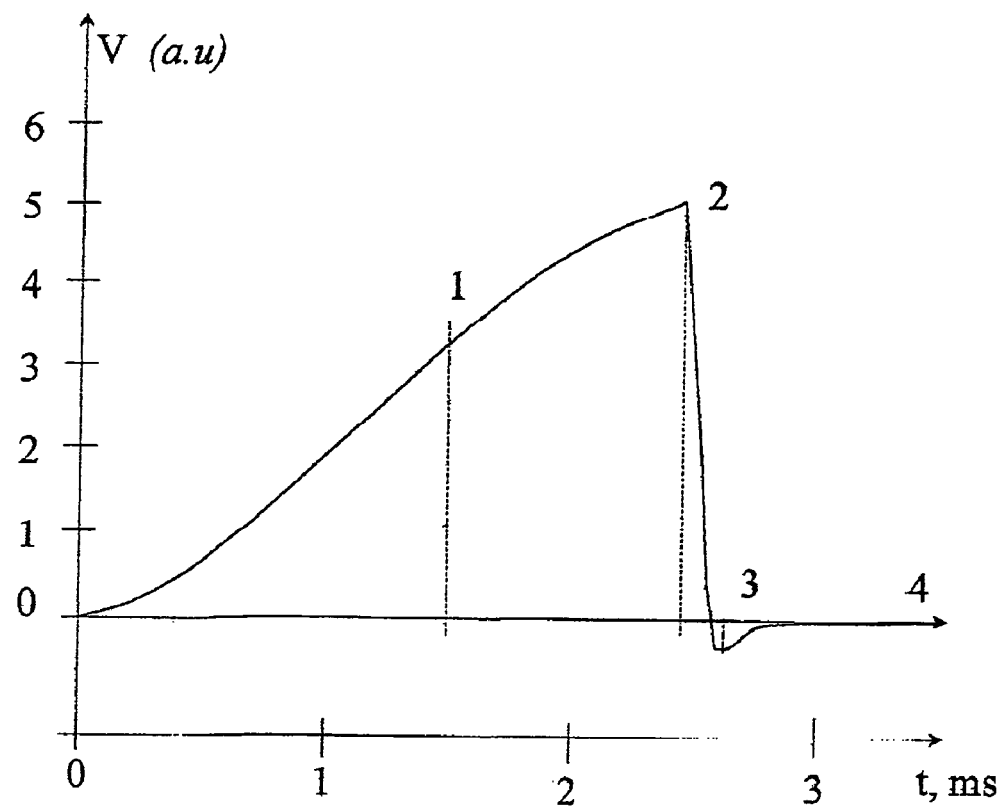
FIG. 2 shows a signal output of the apparatus.
Figure 3A:
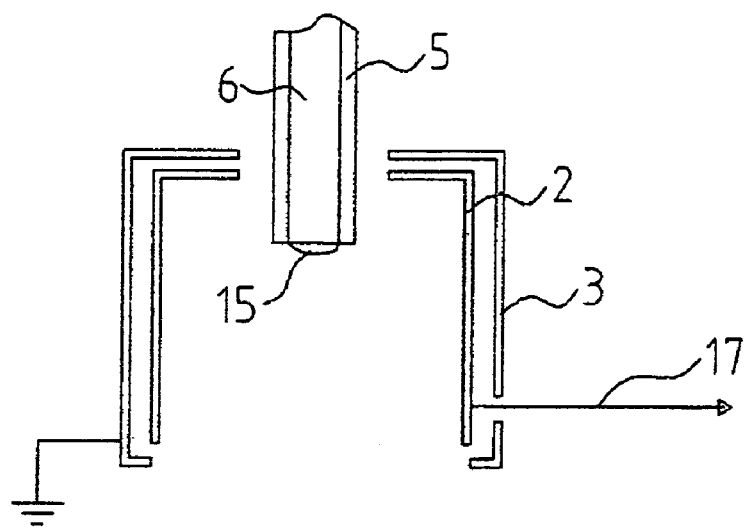
FIG. 3 shows schematically the operation of the apparatus.
Figure 3B:
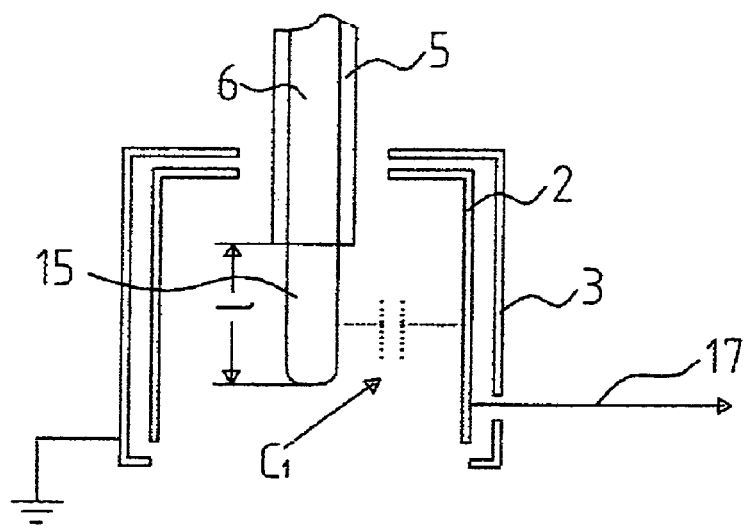
Figure 3C:
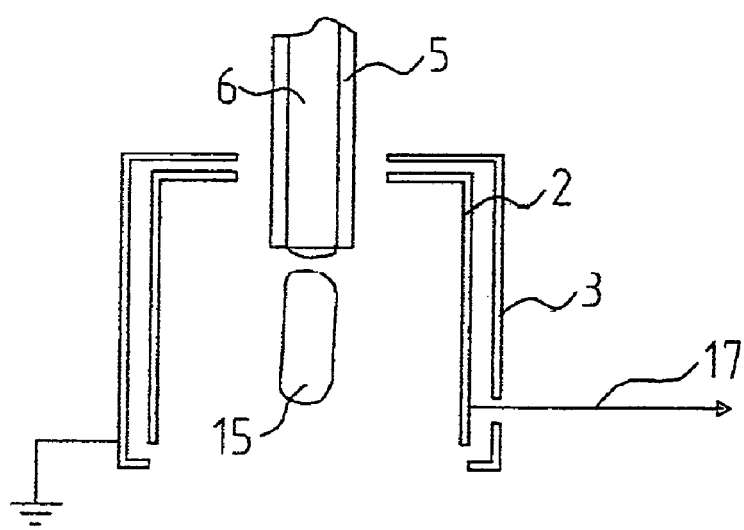

FIG. 2 shows a typical dependency of the output signal voltage V at the output of the apparatus as a function of time t. The volume of the droplet 15 dispensed is around 100 nl. In this example of the use of the apparatus 1, the dispenser used was that disclosed in the specifications of the following patent applications: U.S. patent application Ser. No. 09/709,541, filed 13 Nov., 1990; PCT Application No. PCT/IE02/00039, filed 26 Mar. 2002; and U.S. patent application Ser. No. 09/816,326 filed Mar. 26, 2001, previously referred to. In these specifications, there is described a dispenser having a floating boss which engages and disengages a valve seat to control the amount of liquid dispensed through the nozzle. The liquid dispensed was water. To increase the electrical conductivity of the water, NaCl was added to the water in concentration of some 0.003 kg/liter. The absolute value of the voltage V at the output of the apparatus is irrelevant as it can be boosted by the signal-conditioning amplifier 20 to virtually any value. Therefore, units along the V-axis in FIG. 2 are arbitrary. However, the typical value at the input of the preamplifier 16 is a more relevant indicator. It is in the range of 0.1 to 2V. It should be appreciated that this voltage is also proportional to the voltage at the output of the RF oscillator 10. At the moment 0, the boss of the dispenser opens up and the drop begins to be expelled from the nozzle 5. FIG. 2 is related to the case when the pressure in the dispenser is high enough so that the droplet 15 is expelled in the shape of a cylinder rather than sphere. This is shown in FIGS. 3a, 3b, 3c. The instant corresponding to the point 0 of FIG. 2 is shown in FIG. 3a and the moment corresponding to the point 1 is shown as FIG. 3b. As the droplet essentially forms a conducting rod connected to the dispensing tip 7 of the nozzle 5 and thus to the RF oscillator 10, it changes the capacitance between the nozzle 5 and the inner chamber 2 which acts as an inner electrode. This is shown schematically as a virtual capacitor in dashed lines in FIG. 3b and identified by the arrow $C_1$. At the point 2, the boss closes the dispenser and the supply of liquid required to extend the jet further discontinues. The droplet 15 then gets detached from the nozzle as shown in FIG. 3c. At this moment the additional capacitance, i.e. $C_1$ between the nozzle 5 and the inner chamber 2 disappears and this is represented by the sudden voltage drop as shown by points 2 and 3 in FIG. 2. One can see that the point 3 corresponds to the signal level that is even lower than the one before the dispensation. This is the result of capacitance being reduced compared to the one at point 0 of FIG. 2. This is due to the fact that drop is a conductor that still partly fills the space between the two electrodes of the capacitor: the nozzle and the inner chamber 2, thus reducing capacitance between the two electrodes. One could also say that the drop partly shields the electric field induced by the nozzle at the inner chamber thus reducing capacitance; Effectively it changes the dielectric between the electrodes of the virtual capacitor formed by the nozzle 5 and the inner chamber 2.

As the droplet 15 leaves the inner chamber 2, the signal V increases to the pre-dispensation level as shown by the segment 34 in FIG. 2. In this case, the increase in the capacitance at the point 2 of the curve of FIG. 2 is proportional to its length l. The situation can be represented by the simple model whereby there is a variable capacitor composed of a hollow cylinder representing the inner chamber as one electrode and a rod with the diameter equal to the diameter of the nozzle as the second one located along the axis of the cylinder. The rod can protrude inside the inner chamber thus changing the capacitance of the structure. If the diameter of the central rod is $D_r$, and the inner diameter of the inner chamber is $D_c$, then the additional capacitance by the droplet can be approximated as:

$$C_1 = 2*\pi*\epsilon_o*l/ln(Dc/Dr) \quad (1)$$

Here $\pi=3.1415$ and $\epsilon_o$ is the dielectric constant of the media in which the liquid is being dispensed (air in most cases). The typical values of the capacitance C, are in the range of 0.02 pF to 0.2 pF for the following dimensions: length of the inner chamber 5 mm, diameter of the inner chamber 2 mm, diameter of the nozzle 0.16 mm.

Clearly, this is not a kind of design that would be normally used to construct a variable capacitor, however, the analogy is beneficial to explain the operation of the device.

Figure 4:
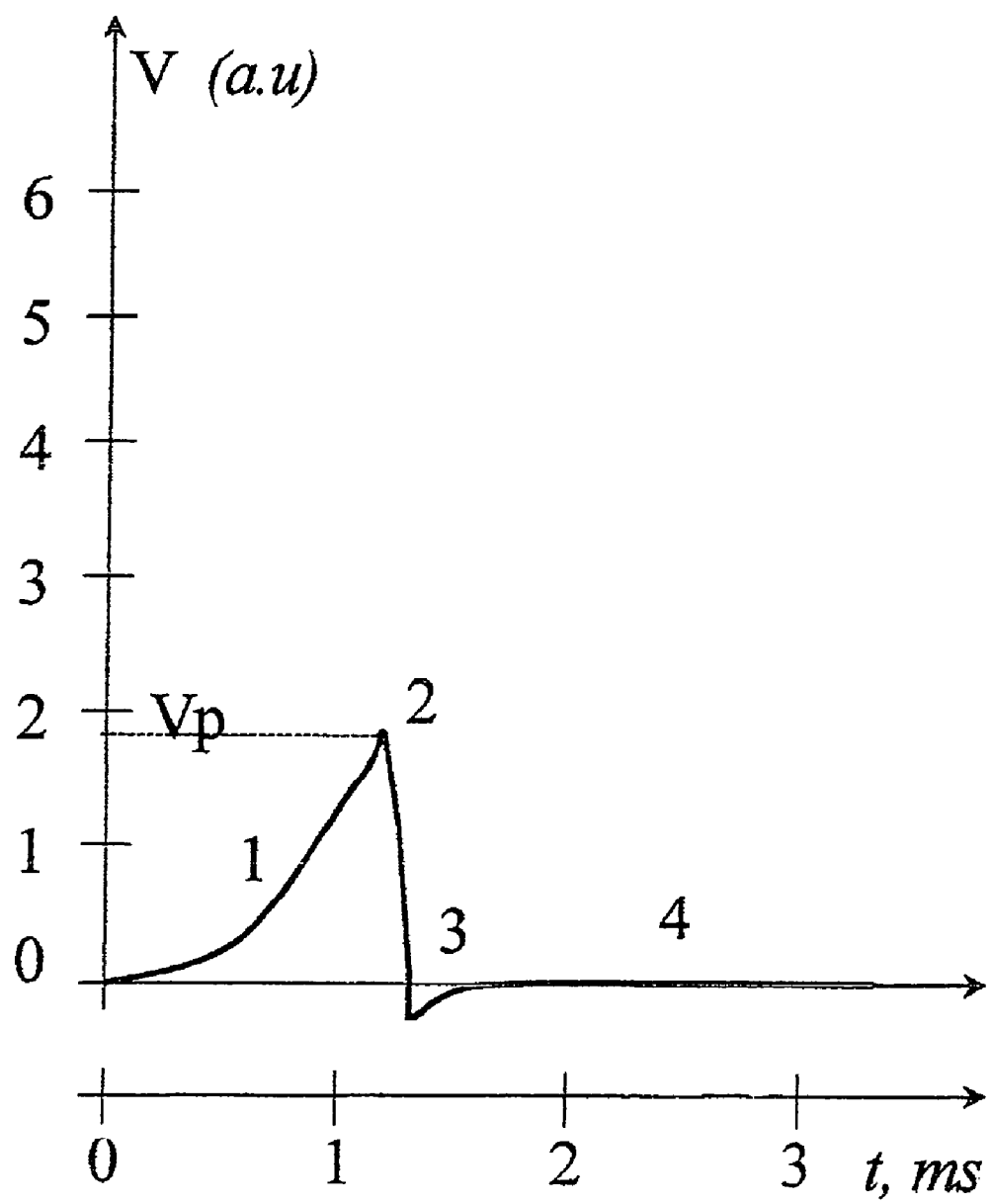
FIG. 4 shows another output signal of the apparatus.

FIG. 4 shows the signal curve for the case when the droplet 15 of a smaller volume is dispensed and the length of the jet segment forming the droplet 15 is therefore small by comparison with the length of the inner chamber. In this case, unlike in FIG. 2, the signal does not reach the saturation level before the drop off moment. It rather reaches a lower level that is indicated by the letter $V_p$ in FIG. 4 and the signal at the point 2 is further away from the saturation level. Numerals on the curve indicating different stages of the dispensation process have the same meaning as in FIG. 2. The drop off moment is marked by the numeral 2.

Figure 5:
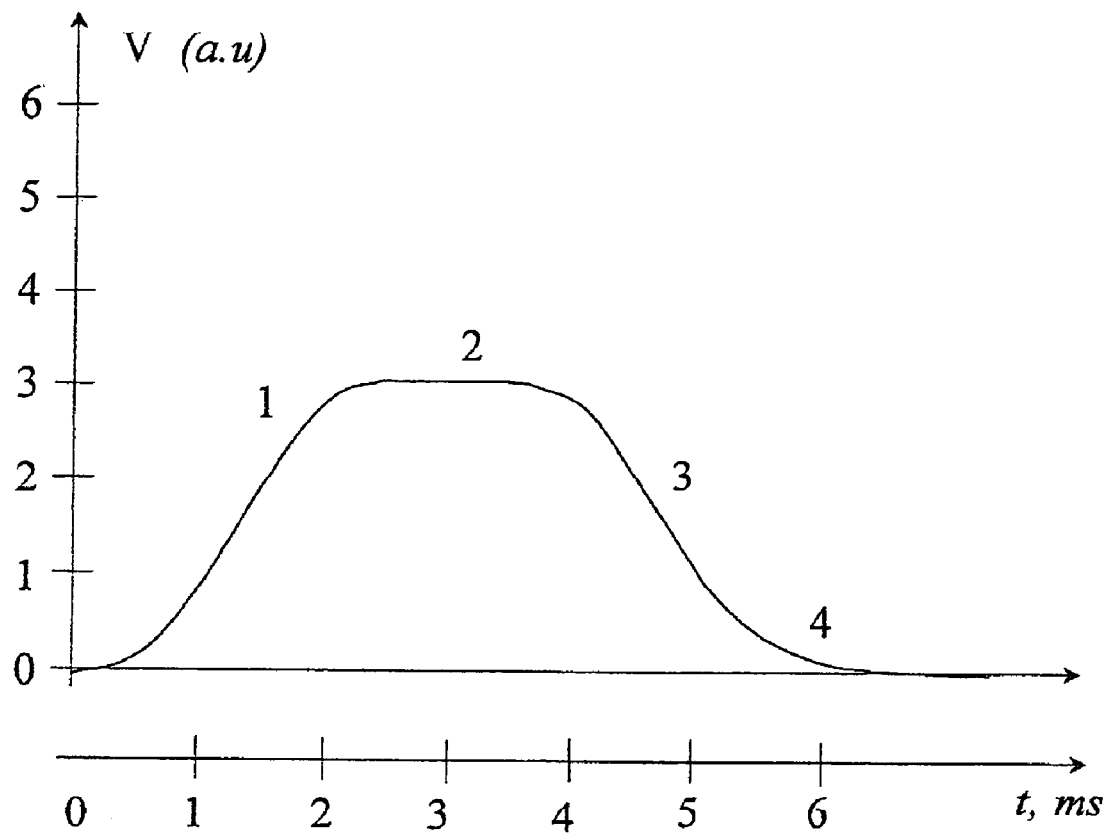
FIG. 5 shows a typical signal induced in a Faraday pail caused by the droplet passing through the pail.

One can appreciate from the above explanation and FIGS. 2 and 4 that the moment of the droplet separation can be monitored by detecting the timing of the falling front in the V(t) curve. FIG. 5 helps explain the difference between the present invention and a Faraday pail. It shows the voltage V induced at the inner chamber during the dispensing in the case of a Faraday pail experiment. FIG. 5 presents results of dispensation in which the drop is formed as a jet that is short enough so that when it gets separated from the nozzle its front end has not reached yet the exit of the inner chamber. In this case the absolute value of the signal at the point 2 (FIG. 5) corresponds to the total charge placed inside the inner chamber and therefore to the total length of the jet segment located inside the inner chamber.

As the drop is leaving the inner chamber, the length of the jet segment in the inner chamber decreases along with the charge placed in it. Therefore, the signal induced in the Faraday pail decreases as shown by the numerals 2-3-4. One can see that the time characteristics of the voltages in FIGS. 4 and 5 differ significantly. The key difference could be summarised as: the Faraday pail is insensitive to the separation of a droplet from the nozzle. The reason is that the separation does not significantly change the charge of the droplet thus the Faraday pail is sensitive to the charge. The difference is also in the fact that according to the present invention, the system for droplet measurements is effectively insensitive to the drop once it has separated from the nozzle even if it is still located inside the inner chamber. On the contrary, the Faraday pail senses the charged drop placed inside the inner chamber regardless of its separation from the nozzle. In the case of results presented in FIG. 5, we used Faraday pail with the following dimensions of the inner chamber: Dc=5 mm, l=10 mm. The value of the signal induced in the Faraday pail depends on the amplifier used. Therefore, the Y-axis in FIG. 5 is marked in arbitrary units. Naturally, by amplifying the voltage, one also amplifies the noise. Therefore, amplifying the voltage beyond certain point does not necessarily improve the sensitivity of the Faraday pail. The noise floor of the conventional Faraday pail is mainly defined by the input noise current and voltage of the amplifier at low frequencies, which could be substantial depending on the specific design.

To complete the comparison of the apparatus of the present invention with a Faraday pail, it is advantageous to consider their sensitivities. Typically a Faraday pail can detect droplets down to 100 nl volume with the voltage of some 20 V applied to the nozzle. An apparatus constructed in accordance with the present invention has, in tests, detected droplets down to 10 nl volume.

For small drops as shown in FIG. 4, one can detect the length of the droplet l from the peak voltage corresponding to the point 2. This can be calculated using the formula (1). The volume v of the droplet can then be calculated if the diameter of the jet $D_n$ is known according to the formula $$v = l * \pi * (D_n/2)^2 \qquad (2)$$

Here $D_n$ is the inner diameter of the nozzle. In our model of the rod protruding inside the cylinder we can suggest that $D_n = D_r$. Alternatively, a more practical solution could be to calibrate the instrument by dispensing initially a number of drops on a microbalance, measure their volume and record the respective amplitude of the voltage $V_p$. The value obtained from this procedure can be tabulated and used later as calibration values.

Figure 6:
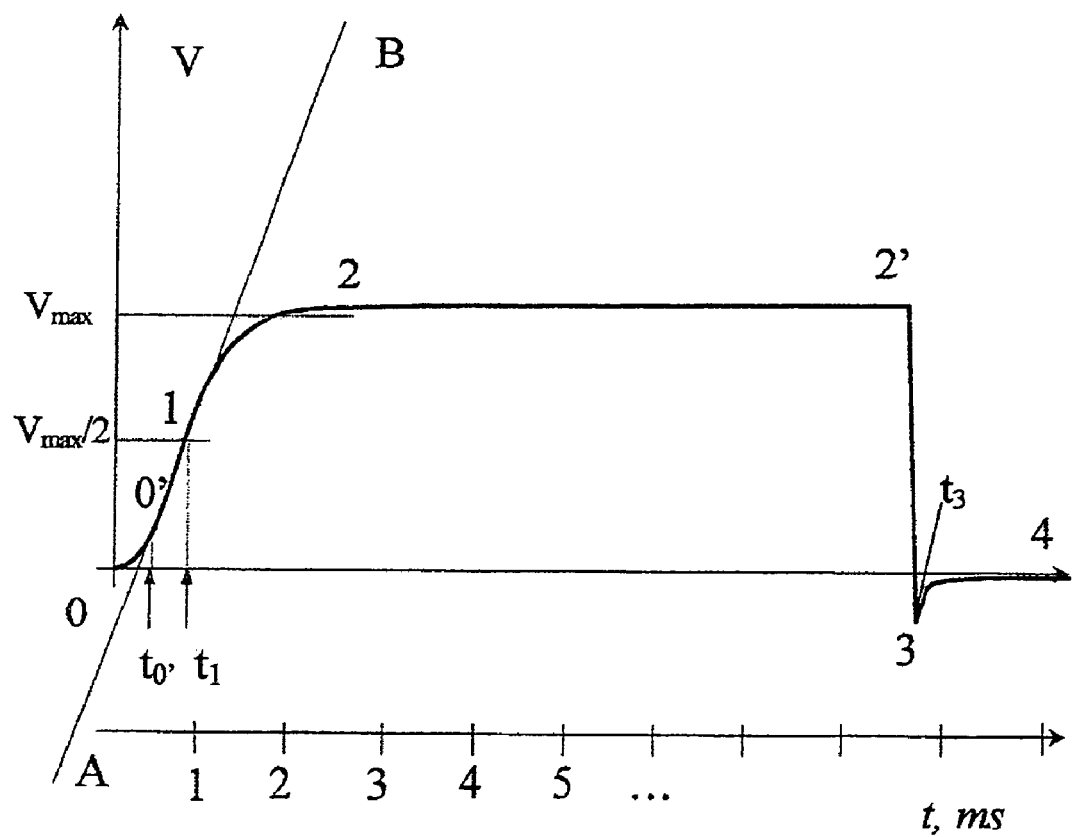
FIG. 6 shows another output signal of the apparatus.

Referring to FIG. 6, even if the droplet extends beyond the extent of the inner chamber, the droplet's volume can still be measured using the current invention. This can then be done by calculating the velocity of the droplet or more properly a drop or jet and the time from the beginning of the dispensation corresponding to the point 0 to the end of the dispensation corresponding to the point 2' as shown in FIG. 6. FIG. 6 corresponds to dispensing of a drop with the volume of 500 nl using the same dispenser with the nozzle having $D_n = 0.16$ mm. At the point 2 when the droplet extends from the nozzle by approx 5 mm the voltage reaches maximum $V_{max}$. Then the voltage does not change any more although the dispensation continues until the moment corresponding to the point 2'. One can appreciate for this situation it may be better to use the term jet instead of the terms "droplet" or "drop". We will use both of these terms below whichever is more appropriate in the context. The total volume of the droplet can be calculated from the graph of FIG. 6 as follows: the dispensation time is equal to $t_3$. If we know the linear velocity $v_j$ of the jet, the length of the jet l can be calculated as $l = v_j * t_3$. The volume of the drop is equal to the length l multiplied by the cross-sectional area of the bore of the nozzle.

The linear velocity $v_j$ of the jet can also be calculated from the graph of the FIG. 6. To understand the procedure, it is necessary to analyse the segment 0-0'-1-2 of the FIG. 6. The initial part of the curve 0-0' is nonlinear. This corresponds to the acceleration of the jet by the pressure as dispensing starts. Around the point 0' the velocity of the jet reaches constant value and from there on the droplet in the form of a jet essentially moves with such constant velocity. This can be determined from the slope of the graph around the point 1 as shown by straight line AB. From this slope, the velocity can be estimated as follows:

$$v_j = (dV/dt) * (l_i/Vmax) \qquad (3)$$

where dV/dt is the slope of the graph at the point 1 and $l_i$ is the length of the inner chamber. Alternatively, the proportionality coefficient between the slope of the graph and the linear velocity of the jet can be verified by means of a calibration procedure using a microbalance. The point 1 is chosen so that it corresponds to the voltage approximately $V_{max}/2$ meaning that the front end of the jet is located approximately in the middle of the inner chamber. At the same time it has to correspond to the linear part of the graph V(t) meaning that the jet has been accelerated to the point of saturation and now moves with constant velocity. One can devise a more complicated algorithm for more accurate calculation of the drop volume. This would take into account the fact that at the initial segment 0-0' the drop moves with a constant acceleration. This acceleration could be approximated as a constant acceleration a. Therefore, strictly speaking the jet moves with a constant velocity during the shorter time interval $t_3 - t_{0'}$ and not $t_3$. Then the length of the jet expelled during the dime $t_{0'}$, called here $l_{0'}$, can be calculated using the formula for movement with constant acceleration: $l_{0'} = (1/2) a * t_{0'}^2$. The acceleration a can again be calculated from the slope of the segment 0-0' of the graph. Alternatively, one could take a different algorithm. During the time interval $t_3 - t_1$ the jet moves with constant velocity and therefore the length of the jet expelled from the nozzle during this interval $l_{t1-t3}$ can be calculated as explained above. At the point $t_1$, the jet is extended through half the length of the inner chamber as explained above. Therefore, the total length of the jet can be estimated as:

$$l = l_i/2 + l_{t1-t3} \qquad (4)$$

The above discussion assumed that the nozzle is inserted at the inner chamber by a distance small by comparison with its length $l_c$. If this is not the case, adjustments need to be made to the formula (4). In a typical embodiment, the nozzle is indeed inserted only by a 1 or 2 mm inside the inner chamber.

In many experiments the complex volume calculation algorithms taking into account acceleration at the segment 0-0' are not necessary and one can separate the dispensation into two distinct cases:

1. The entire segment of the drop is placed inside the inner chamber and therefore the voltage V is smaller than $V_{max}$. In this case the volume can be measured from the value of the voltage V.
2. The jet extends beyond the length of the inner chamber. In this case taking into account movement with acceleration at the initial stage of the dispensing usually only results in small correction and can be disregarded.

A simplified algorithm based on the movement of the movement of the jet with constant velocity is in practice often sufficiently accurate.

It will be noted that once the basic feature of the present invention is appreciated, the manner in which the volume is calculated is such that those skilled in the art can provide many ways of doing it.

The same approach allows detecting leakage from the dispenser. If in the absence of the dispensing, the voltage V remains unchanged this indicates that the dispenser does not leak. Alternatively, if the dispenser leaks, the value of the voltage V changes as the capacitance C changes. One can also detect the moment when the nozzle has been inserted inside the inner chamber, which could be a helpful feature in an automated dispenser.

Figure 7:
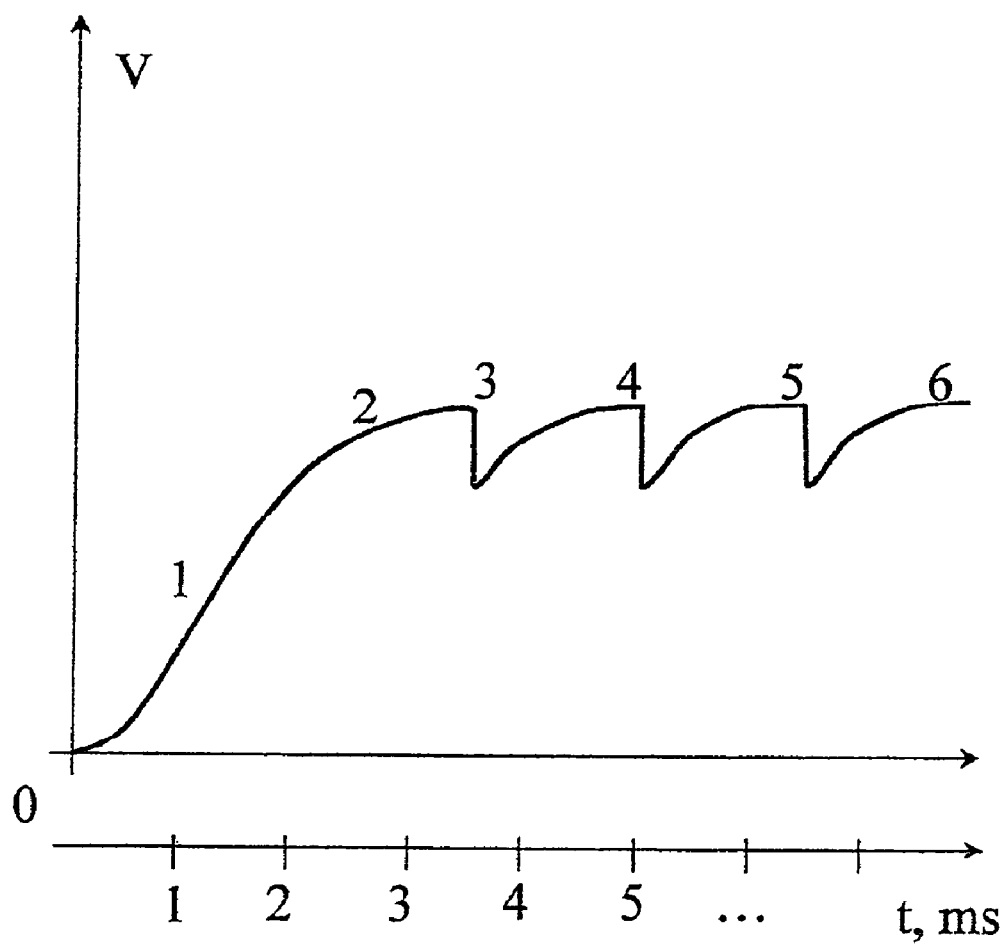
FIG. 7 shows a still further output signal of the apparatus.
Figure 8:
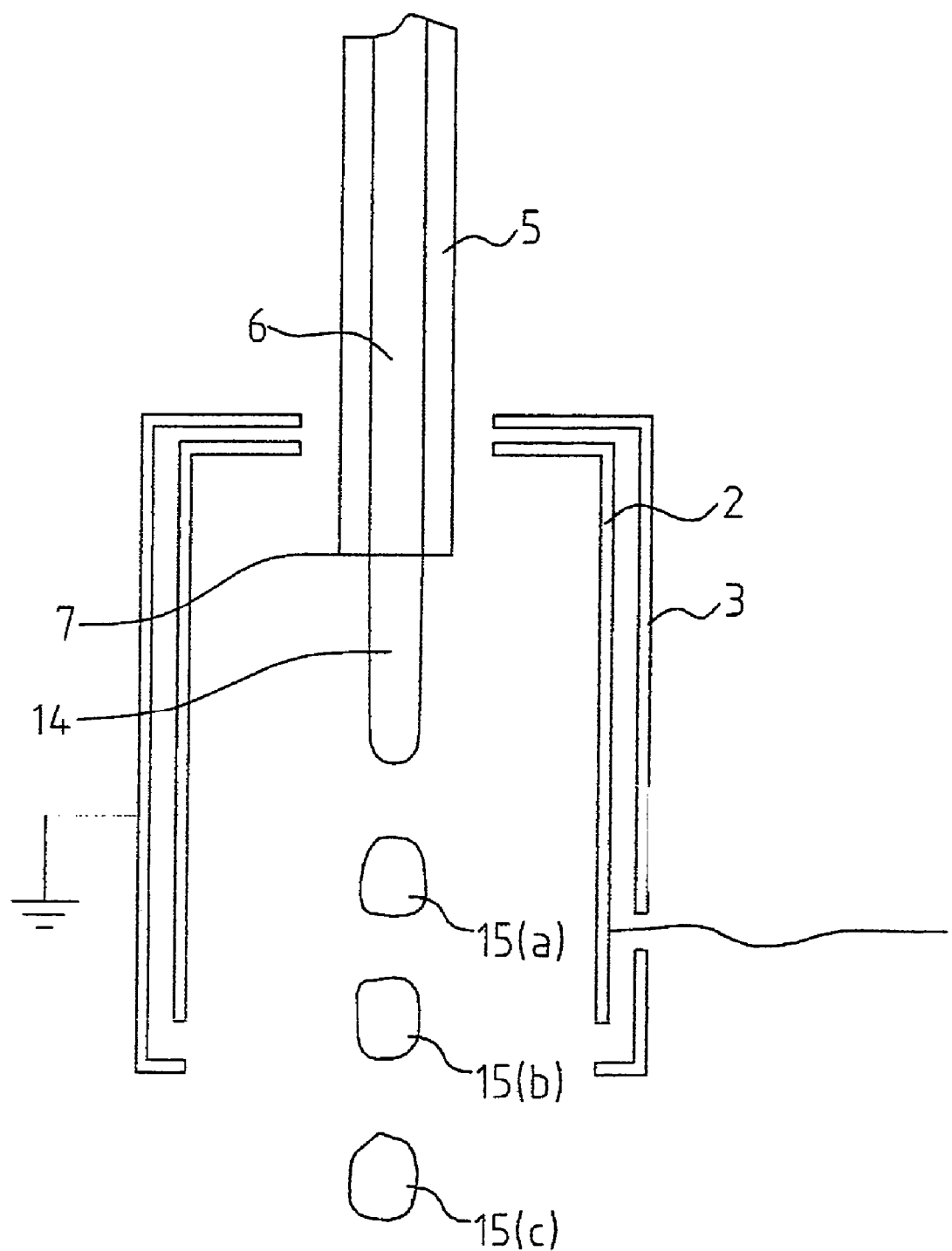
FIG. 8 is a diagrammatic view of the operation of the apparatus to produce the output signal of FIG. 7, FIGS. 9 to 13 are views similar to FIG. 1 of alternative embodiments of the invention.

Referring to FIGS. 7 and 8, there is illustrated the situation where the dispenser is dispensing a relatively low velocity continuous jet, identified by the reference numeral 14. The droplets are still identified by the reference numerals 15 and, where appropriate, suitable letters (a), (b) and (c).

Any jet eventually breaks up under the influence of surface tension into separate droplets. However, the jet breaks up at a shorter distance from the dispensing tip 7 of the nozzle 5 as if it travels with a slower velocity. The jet velocity can be controlled and adjusted by varying the pressure in the dispenser. FIG. 8 shows the case when the jet 14 breaks up inside the inner chamber 2 into separate droplets, identified as 15(a), 15(b) and 15(c): etc. As each droplet becomes separated from the continuous segment of jet 14 at the dispensing tip 7 of the nozzle 5, the capacitance between the nozzle 5 and the inner chamber 2 changes as shown by points 3, 4, 5, etc in FIG. 7. This is caused by the reduction in capacitance caused by the formation of droplets electrically disconnected from each other. Therefore, the apparatus can be used to analyse the process of breaking the jet 14 into separate droplets 15. This is a useful tool for optimising the jet velocity in a dispenser. If the jet velocity is too high, it produces splashes as it comes in contact with the destination substrate. If on the other hand the jet velocity is too low, the accuracy of the dispensing could be compromised through the creation of instabilities, drops hanging at the end of the nozzle, etc. In this way, the characteristics of the droplet can be accurately ascertained both in their frequency and in their volume. Thus, if the droplets are being dispensed automatically, for example, onto a substrate by traversing the substrate, this can be accurately controlled. The term "characteristics", as used here, therefore refers not just simply to the volume of the droplet but also to the frequency at which the droplets are being ejected or formed. It will be appreciated that it can be easily seen how this can be ascertained. For example, if you know the frequency of break-up of the droplets, it is easy to control the deposition of the droplets. Further, the pressure at which the jet is being ejected can be accurately controlled to achieve formation of a stable jet.

Figure 9:
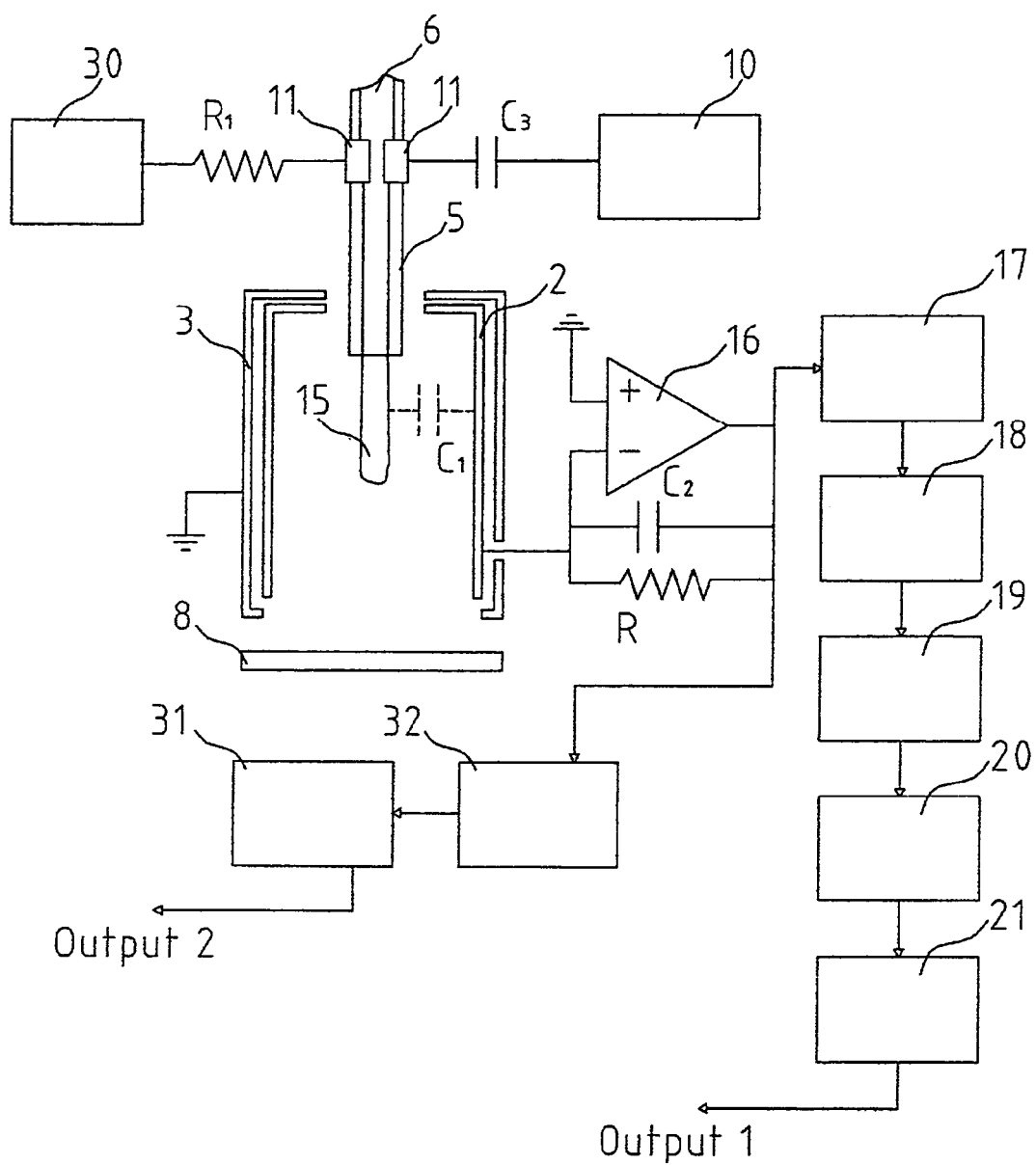

Referring to FIG. 9, there is illustrated the use of the invention in combination with a Faraday pail. Pails similar to those described with reference to FIG. 1 are identified by the same reference numerals. The RF oscillator 10 is connected to the electrode 11 through a capacitor $C_3$ (some 1000 pF or more) to avoid applying DC voltage to the RF oscillator 10. The RF oscillator 10 generates voltage at the frequency $f_0$ of some 0.1 to 1 MHz with the amplitude of some 0.1 to 1 V. A separate DC voltage source 30 generating voltage of some 5 to 40 V is also connected to the electrode 11 through a resistor $R_1$ having a resistance of some 10 kOhm. The purpose of the resistor $R_1$ is to separate the DC and AC sources from each other. The inner chamber 2 is connected to a preamplifier, indicated generally by the reference numeral 16. The preamplifier 16 consists of a high-speed operational amplifier with low bias current such as OPA111/OPA604 (Texas Instruments) or another suitable one using the feedback composed of a capacitor $C_2$ (10 pF) and a resistor R (some $10^9$ Ω or 1 GOhm). The output from the preamplifier 16 is sent to the band pass filter 17 with the follow up circuit as in FIG. 1, and also it is sent to a signal conditioning circuit 31 though a low pass filter 32. The band pass filter 17 passes through frequencies around $f_0$, the frequency of the RF oscillator 16. From the band pass filter 17 the signal is sent to the rectifier 18, low pass filter 19 and signal conditioning amplifier 20. The final output, identified as the output 1, then gives the signal as described in the present specification that is sensitive to the capacitance change caused by the droplet dispensation. The outer output or output 2 gives the signal that is sensitive to the charge of the droplet, i.e. the Faraday pail output. The gain of the preamplifier 16 according to the present invention is proportional to the ratio of $C_1/C_2$ where $C_1$ is the capacitance change caused by the droplet in the inner chamber. The latter is schematically indicated in FIG. 9. Therefore, the capacitance $C_2$ should preferably be rather small. A value for $C_2$ in the range of 1 to 10 picoFarad has been found to be convenient. The value of the resistor $R_2$ should preferably be different when operating the instrument in the Faraday pail mode or in the mode of measuring the capacitance $C_1$ as in accordance with the present invention. When operating the instrument in the Faraday pail mode, the resistor R is required to allow the inner chamber 2 to discharge after the dispensing so that it does not accumulate excessive amount of charge. Typical value of R=50 GOhm is adequate for the measurements made in the Faraday pail mode. Significantly smaller resistance is often undesirable as it may lead to leakage of the current induced in the inner chamber 2 by the droplet 15. For RF capacitance measurements in accordance with the invention, the typical value of the resistance is in the range of 2 to 100 MOhm. Therefore, the resistor $R_2$ is in fact formed by one of two resistors. The resistor $R_2$ with larger resistance can be connected in parallel with $C_2$ for operation of the apparatus in the Faraday pail mode and the one with smaller resistance can be connected for operation in the mode in accordance with the present invention. The switch selecting the two resistors is not shown in FIG. 9 as it is obvious to those skilled in the art of circuit design.

The choice of the frequency $f_0$ of the RF oscillator 10 requires some discussion. The higher the frequency, the faster the measurement apparatus could function. This is because the signal bandwidth of the instrument could not be made greater than the frequency of the oscillator $f_0$ divided by a factor of some 3 to 10. On the other hand electrical resistance of liquids at high frequencies begins to increase and therefore the efficiency of the signal coupling to the drop is reduced affecting the performance of the apparatus. This implies that a compromise value must be found to satisfy these two requirements. We have found that for water-based liquids, the convenient frequency range is from 100 KHz to some few MHz.

The cut-off frequency of the low-pas filter 19 is set up so that it passes the low frequency band corresponding to the useful signal bandwidth and yet cuts any signal at the frequency $f_0$ and its higher harmonics. The acceptable value for the cut-off frequency is a compromise between the time resolution in the capacitance measurement, the signal noise and the RF oscillator frequency.

Typical bandwidth of the low pas filter 19 is 1 to 50 kHz.

It will be appreciated that the advantage of using what is effectively the technique employed in a Faraday pail, in combination with the present invention, is that the volume of the liquid can be calculated by two methods and if there should be a variance between the calculated volume, i.e. if they exceed a preset amount, it will act as a check on the operation of the apparatus. Such a variance would indicate a possible malfunction which may be recorded and subsequently investigated.

Figure 10:
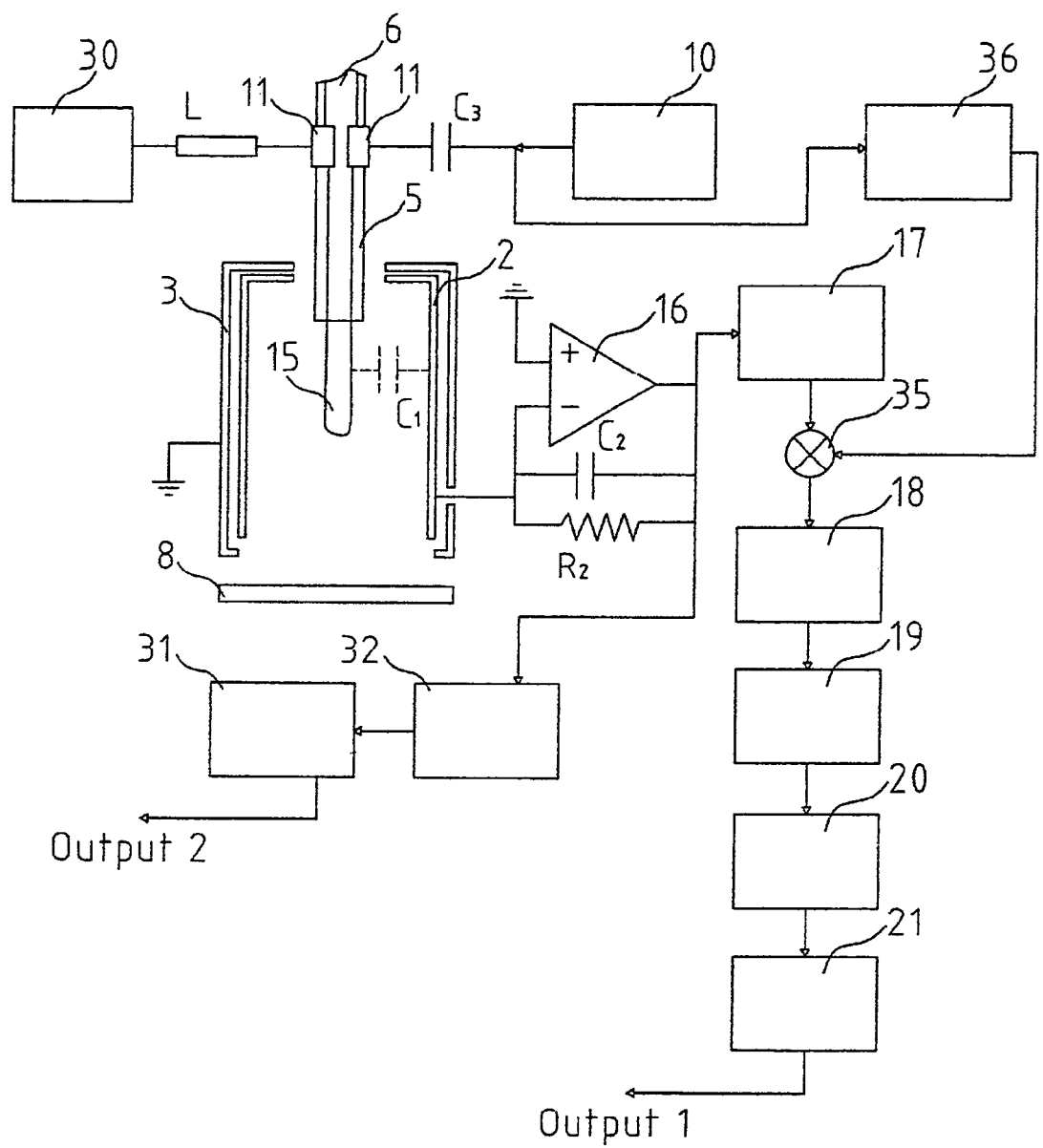

FIG. 10 shows a modification of the circuit of FIG. 9 and the same reference numerals are used in both Figs. It differs from the circuit shown in FIG. 9 in one significant aspect: the amplitude modulated signal at the frequency $f_0$ is demodulated using a phase sensitive detector 35 (lock-in amplifier). The phase sensitive detector 35 in this circuit is installed in between the band pass filter 17 and the low pass filter 18. The phase sensitive detector 35 receives the phase signal from the RF oscillator. This is supplied through a phase shifter 36 as common for circuits utilising phase sensitive detectors and will be appreciated by those skilled in the art of circuit design. Like the circuit of FIG. 9, the circuit shown in FIG. 10 also has the output 2 that is sensitive to the charge carried by the droplet. This method improves the signal-to-noise performance.

Figure 11:
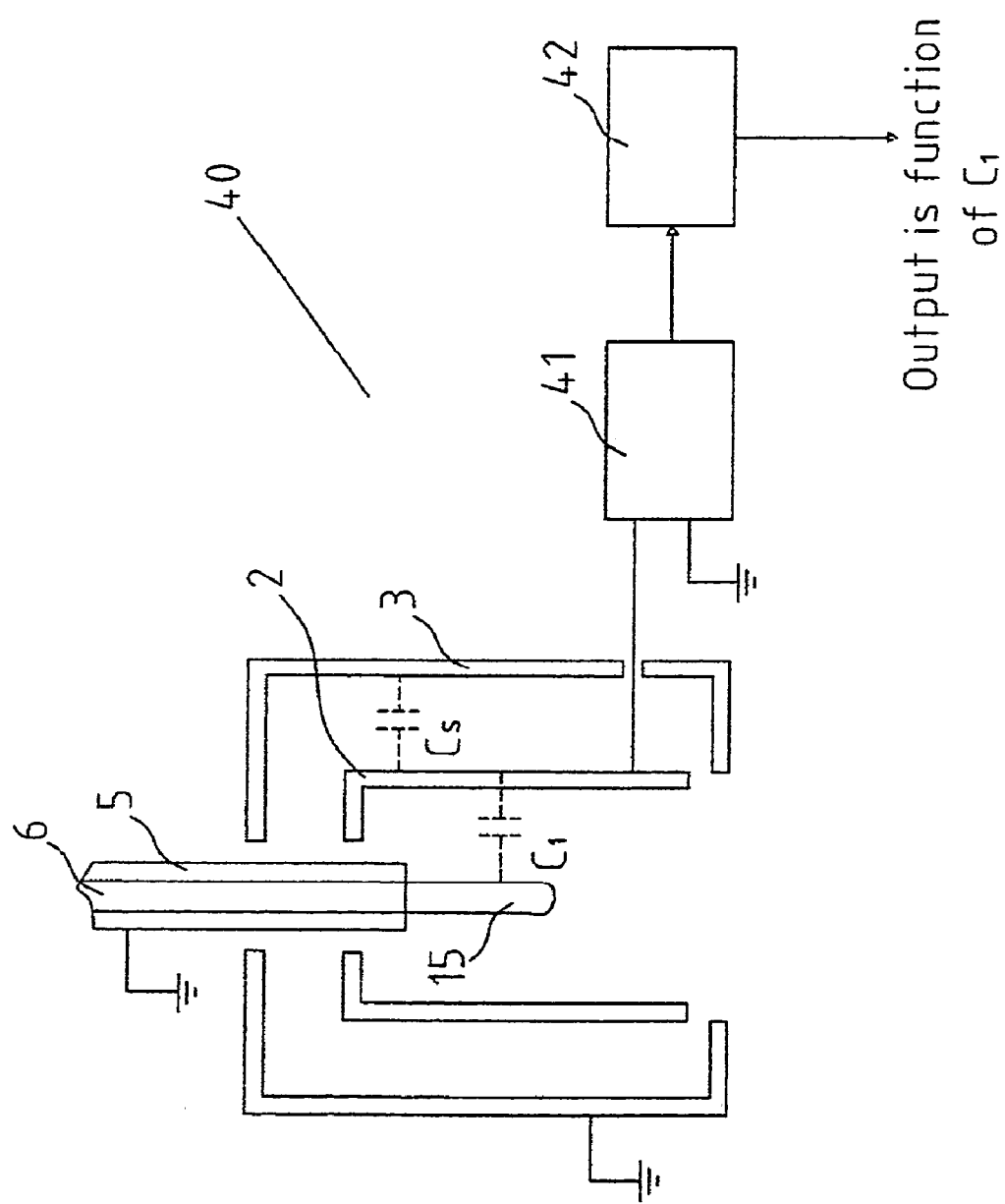

Referring to FIG. 11, there is illustrated an alternative construction of apparatus indicated generally by the reference numeral 40 in which parts similar to those of the previous embodiments are identified by the same reference numerals. There is provided a parametric RF oscillator 41, namely an oscillator whose frequency is dependent on the value of capacitance connected to the input of the instrument. The RF oscillator 41 is connected to the inner chamber 2. The nozzle 5 in this embodiment is connected to the ground potential. The effective capacitance coupled to the input of the parametric oscillator is normally equal to $C_s$ which is the capacitance between the inner chamber 2 and outer shield 3, the capacitance of the cables, and the capacitance of the nozzle 5 inserted in the inner chamber 2. This virtual capacitance $C_s$ is shown by dashed lines. During the droplet dispensation, an additional capacitance $C_1$ arises as shown in FIG. 11 by dashed lines thus causing a frequency shift in the RF oscillator 41. The output of the parametric oscillator 41 is coupled to a frequency demodulation circuit 42. The output of the frequency demodulation circuit 42 gives the frequency of the parametric oscillator 41, which is indicative of the value of capacitance $C_1$. The droplet measurement apparatus needs to be calibrated in the manner similar to the calibration routine described above: the frequency change needs to be monitored and the volume of the droplet dispensed needs to be measured using e.g. a microbalance.

Figure 12:
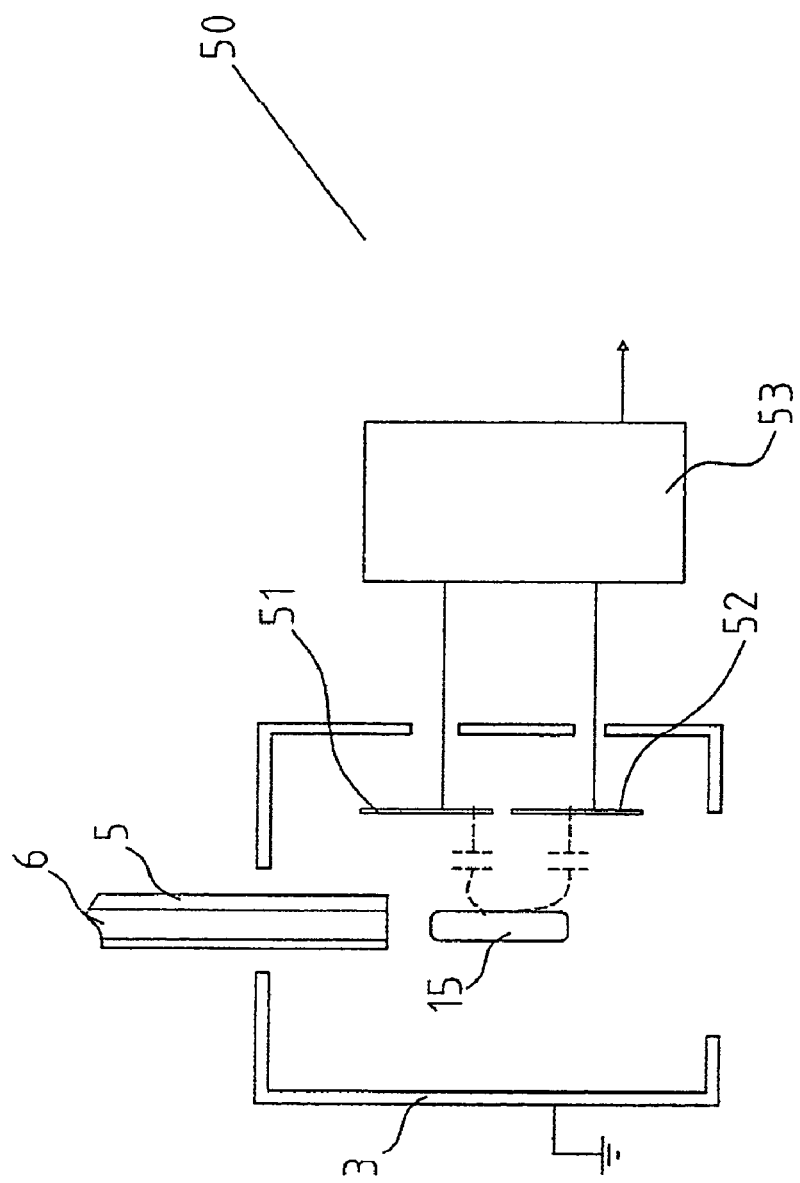

FIG. 12 shows another embodiment of the droplet measurement apparatus, identified generally by the reference numeral 50. In this embodiment the inner chamber 2 is arranged to form two plates 51 and 52, in turn forming two electrically conducting electrodes, coupled to a capacitance measurement circuit 53. The capacitance measurement circuit could be similar to the one shown in FIG. 11. For example it could consist of a parametric oscillator and the frequency demodulation circuit. The capacitance between the electrodes formed by the plates 51 and 52 is altered when a droplet passes in their vicinity. Effectively, the droplet alters the dielectric constant of the medium in the vicinity of the plates of the capacitor. The rest of the operation of this embodiment is similar to the one described in FIG. 11. In this embodiment the liquid dispensed does not have to be conducting. This embodiment is thus suited for measurement of droplets of non-conducting liquids. Generally the apparatus has greater sensitivity to liquids with large dielectric constants.

Figure 13:
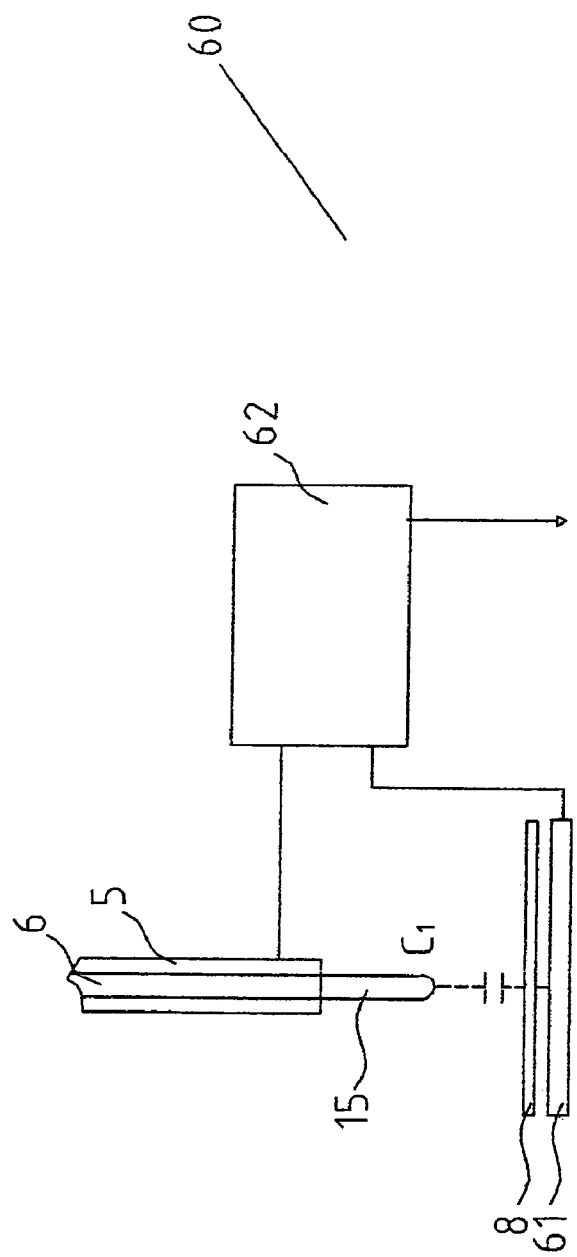

FIG. 13 shows another apparatus, indicated generally by the reference numeral 60, with parts similar to those previously described identified by the same reference numerals. In this embodiment there is an electrically conducting electrode plate 51 positioned underneath the destination substrate. Essentially, this is a modification of the embodiment of FIG. 12 in which the nozzle 5 and the electrode plate 51 function as plates 51 and 52 to form two electrodes. They are connected to a fast impedance measurement circuit 62. This embodiment measures the capacitance between the nozzle 5 and the electrode plate 61. At the moment when a jet 14 protrudes from the nozzle 5 towards the destination substrate 8, the capacitance increases. This virtual capacitance is shown in FIG. 13 by dashed lines and the letter C1. Once the jet gets detached from nozzle, the capacitance decreases again. This embodiment works best with electrically conducting liquids. The fast impedance measurement circuit could be the same as the capacitance measurement circuit of FIG. 12, i.e. it could be based on a parametric oscillator. Alternatively one could utilise the approach shown in FIG. 9. In this case the RF signal at the frequency $f_0$ could be coupled to the nozzle and the detection preamplifier could be coupled to the electrode plate. The preamplifier with the band pass filter and rectifier serves then to measure the amplitude of the signal at the frequency $f_0$. Alternatively to measure the signal at the frequency $f_0$ one could utilise the circuit of FIG. 10.

Figure 14:
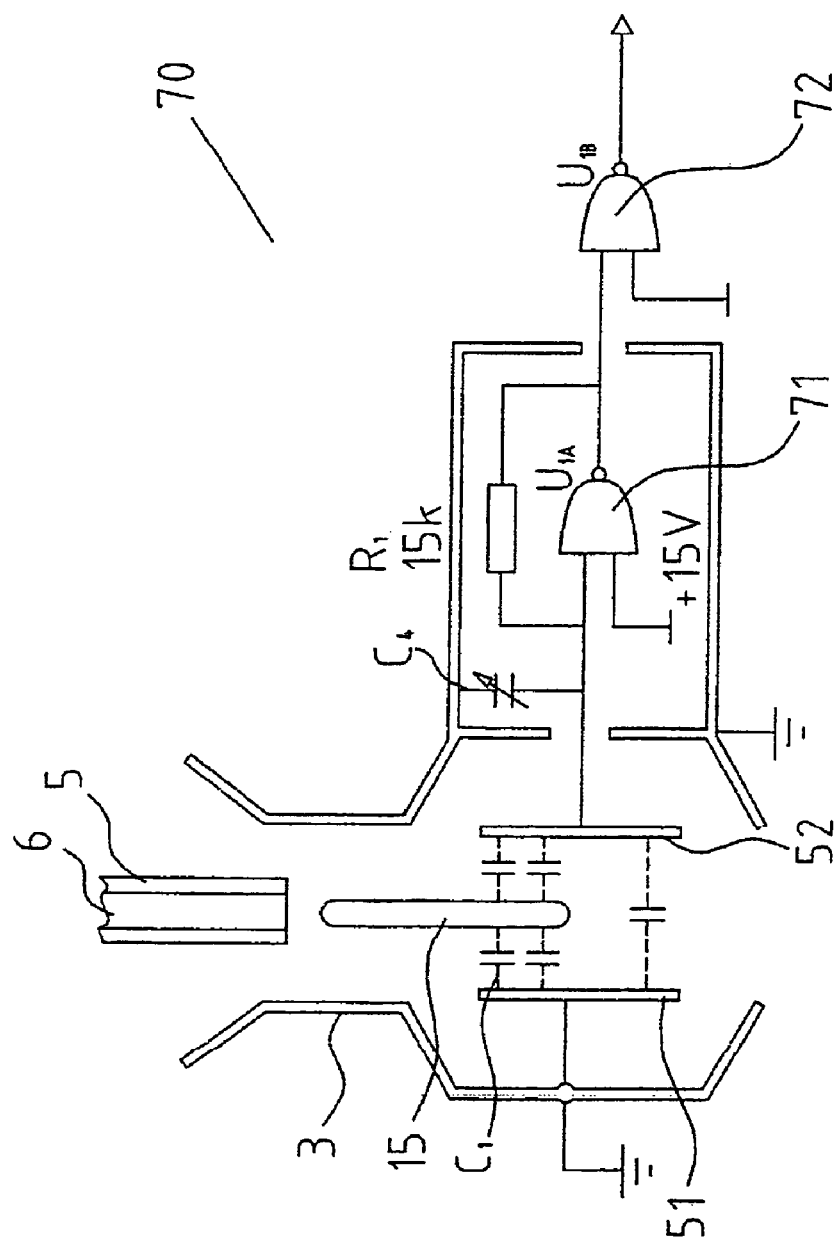
FIG. 14 is a diagrammatic representation of an alternative apparatus for carrying out the invention.

FIG. 14 is another apparatus incorporating a parametric oscillator for use in the present invention. The apparatus of FIG. 14 is somewhat similar in construction to that of FIG. 12 and similar parts are identified by the same reference numerals. The parametric oscillator, indicated generally by the reference numeral 70, comprises an inverter 71 (Inverter CD4093B (Fairchild)). A capacitor $C_4$ has a capacitance of some 5-60 pF is inserted at the input of the inverter 71 to make its operation more stable. A second inverter 72 (CD4093B Fairchild) is inserted at the output of the inverter 71 to decouple the inverter 71 from the load and to make its operation more stable. The output of the inverter U1B is a digital waveform with a frequency close to 1 MHz. The frequency is then divided down to some 5-50 kHz by a simple digital counter and can be measured with a time-to-digital converter. This could be the circuit TDC-GP1 from Acam-Messelectronic GmbH (www.acam.de). This circuit is a fast and sensitive frequency measurement device.

To avoid contaminating the dispenser with liquids, a disposable insert could be installed inside the inner chamber 2 of the drawings. This could be designed to be either non-conducting or conducting. In the later case the insert effectively composes the part of the inner chamber and it should be electrically connected to it.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiment hereinbefore described, but may be varied in both construction and detail within the scope of the appended claims.

The invention claimed is:

1. A method of monitoring and measuring the volume of a liquid droplet as it is being discharged from a liquid dispensing system comprising a nozzle having a dispensing tip, the method comprising:
    using the liquid to form at least part of one of the three components of a capacitor, namely, the dielectric and the two separate electrically conductive members; and
    measuring the change in capacitance in the capacitor so formed as the liquid is discharged from the nozzle, whereby the volume of liquid dispensed and the termination of the discharge may be recorded,
    and further comprising:
    electrically energising the liquid with AC current; and
    measuring the capacitance induced in an electrically conductive member sited adjacent the tip as the liquid is being discharged from the nozzle.

2. A method as recited in claim 1, in which the liquid droplet forms one of the electrically conducting members of the capacitor.

3. A method as recited in claim 1, in which the liquid droplet forms a dielectric member positioned in the vicinity of electrically conducting members of the capacitor and altering the effective dielectric constant of the capacitor.

4. A method as recited in claim 1, in which when the liquid and nozzle are of high electrical conductivity, there is provided an electrode remote from and beneath the nozzle, the nozzle and electrode forming plates for the capacitor whereby the growth of a droplet on the dispensing tip increases the capacitance until it drops on detachment of the droplet from the dispensing tip.

5. A method as recited in claim 1, in which when the liquid is a water based liquid, the liquid is energized at a carrying frequency ($f_o$) of between 100 KHz and 5 MHz.

6. A method as recited in claim 1, in which when the liquid is a water based liquid, the liquid is energized at a carrying frequency ($f_o$) of between 0.1 KHz and 1 MHz.

7. A method as recited in claim 1, in which the liquid is energized with both AC and DC current and the volume of the liquid is calculated from both the change in capacitance and the charge carried by the liquid droplet.

8. A method as recited in claim 7, in which when the variance between the calculated volumes exceeds a preset amount, a possible malfunction is recorded.

9. A method as recited in claim 1, in which the initial calibration step is performed of:
    dispensing initially a plurality of droplets;
    measuring the change in capacitance;
    weighing the droplets; and
    storing the data for subsequent use.

10. A method as recited in claim 1, in which the liquid is delivered from the nozzle in a continuous jet and the jet forms separate droplets remote from the dispensing tip while still maintaining the jet, the method further comprising measuring the change in capacitance caused by the jet immediately before and after the formation of a droplet to determine the volume and other characteristics of the droplet.

11. A method as recited in claim 10, in which the information on the characteristics of the droplets is used to control the manner in which the jet is formed.

12. A method as recited in claim 1, in which when liquid is not being discharged from the apparatus, the capacitance is measured and monitored to provide an indication of a possible leak in the apparatus on a change in capacitance being detected.

13. A method of monitoring and measuring liquid discharged from a nozzle having a dispensing tip comprising:
  electrically energising the liquid with AC current; and
  measuring the capacitance induced in an electrically conductive member.

14. A method as recited in claim 13, in which when the liquid and nozzle are of high electrical conductivity, there is provided an electrode remote from and beneath the nozzle, the nozzle and electrode forming plates for the capacitor whereby the growth of a droplet on the dispensing tip increases the capacitance until it drops on detachment of the droplet from the dispensing tip.

15. A method as recited in claim 13, in which when the liquid is a water based liquid, the liquid is energized at a carrying frequency ($f_o$) between 100 KHz and 5 MHz.

16. A method as recited in claim 13, in which when the liquid is a water based liquid, the liquid is energized at a carrying frequency ($f_o$) between 0.1 KHz and 1 MHz.

17. A method as recited in claim 13, in which the liquid is energized with both AC and DC current and the volume of the liquid is calculated from both the change in capacitance and the charge carried by the liquid droplet.

18. A method as recited in claim 17, in which when the variance between the calculated volumes exceeds a preset amount, a possible malfunction is recorded.

19. A method as recited in claim 13, in which the initial calibration step is performed of: dispensing initially a plurality of droplets; measuring the change in capacitance; weighing the droplets; and storing the data for subsequent use.

20. A method as recited in claim 13, in which the liquid is delivered from the nozzle in a continuous jet and the jet forms separate droplets remote from the dispensing tip while still maintaining the jet, the method further comprising measuring the change in capacitance caused by the jet immediately before and after the formation of a droplet to determine the volume and other characteristics of the droplet.

21. A method as recited in claim 20, in which the information on the characteristics of the droplets is used to control the manner in which the jet is formed.

22. A method as recited in claim 13, in which when liquid is not being discharged from the apparatus, the capacitance is measured and monitored to provide an indication of a possible leak in the apparatus on a change in capacitance being detected.

23. A method of monitoring and measuring liquid as it is being discharged from a nozzle having a dispensing tip comprising:
  siting the nozzle within a conductive chamber having an outlet to allow the passing of the liquid therethrough from the nozzle dispensing tip;
  energising the liquid being dispensed by applying a voltage at a preset carrying frequency ($f_0$); and
  measuring the capacitance induced by the interaction of the liquid and the chamber until the liquid detaches from the nozzle.

24. A method as recited in claim 23, in which when the liquid and nozzle are of high electrical conductivity, there is provided an electrode remote from and beneath the nozzle, the nozzle and electrode forming plates for the capacitor whereby the growth of a droplet on the dispensing tip increases the capacitance until it drops on detachment of the droplet from the dispensing tip.

25. A method as recited in claim 23, in which when the liquid is a water based liquid, the liquid is energized at a carrying frequency ($f_o$) between 100 KHz and 5 MHz.

26. A method as recited in claim 23, in which when the liquid is a water based liquid, the liquid is energized at a carrying frequency ($f_o$) between 0.1 KHz and 1 MHz.

27. A method as recited in claim 23, in which the liquid is energized with both AC and DC current and the volume of the liquid is calculated from both the change in capacitance and the charge carried by the liquid droplet.

28. A method as recited in claim 27, in which when the variance between the calculated volumes exceeds a preset amount, a possible malfunction is recorded.

29. A method as recited in claim 23, in which the initial calibration step is performed of: dispensing initially a plurality of droplets; measuring the change in capacitance; weighing the droplets; and storing the data for subsequent use.

30. A method as recited in claim 23, in which the liquid is delivered from the nozzle in a continuous jet and the jet forms separate droplets remote from the dispensing tip while still maintaining the jet, the method further comprising measuring the change in capacitance caused by the jet immediately before and after the formation of a droplet to determine the volume and other characteristics of the droplet.

31. A method as recited in claim 30, in which the information on the characteristics of the droplets is used to control the manner in which the jet is formed.

32. A method as recited in claim 23, in which when liquid is not being discharged from the apparatus, the capacitance is measured and monitored to provide an indication of a possible leak in the apparatus on a change in capacitance being detected.

* * * * *